(12) United States Patent
Hansen

(10) Patent No.: US 6,953,683 B2
(45) Date of Patent: Oct. 11, 2005

(54) COMPOSITIONS AND METHODS OF INHIBITING BACTERIAL SPORE GERMINATION

(75) Inventor: J. Norman Hansen, Silver Spring, MD (US)

(73) Assignee: University of Maryland, College Park, MD (US)

( * ) Notice: Subject to any disclaimer, the term of this patent is extended or adjusted under 35 U.S.C. 154(b) by 304 days.

(21) Appl. No.: 10/299,064

(22) Filed: Nov. 19, 2002

(65) Prior Publication Data

US 2004/0023868 A1 Feb. 5, 2004

Related U.S. Application Data

(63) Continuation-in-part of application No. 09/462,478, filed as application No. PCT/US98/14547 on Jul. 17, 1998, now Pat. No. 6,541,607.
(60) Provisional application No. 60/053,035, filed on Jul. 18, 1997.

(51) Int. Cl.[7] .................................................. C12N 1/12
(52) U.S. Cl. ................................ 435/252.1; 435/252.3; 435/172.3; 435/7.1; 530/350; 530/300; 530/324
(58) Field of Search ......................... 435/252.1, 252.3, 435/172.3, 7.1; 530/350, 300, 324

(56) References Cited

U.S. PATENT DOCUMENTS

| | | |
|---|---|---|
| 4,716,115 A | 12/1987 | Gonzalez et al. |
| 5,218,101 A | 6/1993 | Hansen |
| 5,516,682 A | 5/1996 | Hansen |
| 5,576,420 A | 11/1996 | Hansen |
| 5,861,275 A | 1/1999 | Hansen |
| 5,885,811 A | 3/1999 | Hansen |
| 6,153,405 A | * 11/2000 | Hansen ...................... 435/69.1 |

FOREIGN PATENT DOCUMENTS

WO    WO 00/39152    7/2000

OTHER PUBLICATIONS

U.S. Appl. No. 60/215,449, filed Jun. 29, 2000, Hansen.
Hansen, "Nisin and Related Antimicrobial Peptides", Biotechnology of Antibiotics, Second Edition, Revised and Expanded, pp. 437–467.
Paik, S.H., et al. Isolation and Characterization of Chemical, Physical, and Biological Properti s of Sublancin 168, a Novel Lantibiotic; and the Cloning and Sequencing of the Structural G n of Sublancin 168 and its Transporter Protein. Dissertation Abstracts International. Jan. 1997, vol. 58, 11B, p. 5800.
Chakicherla, et al., "Role of the Leader and Structural Regions of Prelantibiotic Peptides as Assessed by Expressing Nisin–Subtiliin Chim ras in Bacillus subtilis 168, and Characterizati n of Their Physical, Chemical, and Antimicrobial Properties", Journal f Biol. Chemistry, Oct. 1995, vol. 270, No. 40, pp. 23533–23539.

* cited by examiner

*Primary Examiner*—Jon Weber
*Assistant Examiner*—Hope Robinson
(74) *Attorney, Agent, or Firm*—Arent Fox

(57) ABSTRACT

The present invention is directed to compositions comprising nisin and sublancin in amounts that are effective to inhibit bacterial spore germination. Additionally, the present invention is directed towards methods of inhibiting bacterial spore germination for a variety of purposes.

13 Claims, No Drawings

COMPOSITIONS AND METHODS OF INHIBITING BACTERIAL SPORE GERMINATION

This application is a continuation-in-part of U.S. patent application Ser. No. 09/462,478 filed Apr. 17, 2000, now U.S. Pat. No. 6,541,607, which in turn is a national stage entry of PCT Application No. PCT/US98/14547 filed Jul. 17, 1998, which claims the benefit of U.S. Provisional Patent Application No. 60/053,035 filed Jul. 18, 1997. The disclosures of the prior applications are hereby incorporated by reference herein in their entirety.

FIELD OF THE INVENTION

The invention relates to novel compositions and methods of inhibiting the germination of bacterial spores.

BACKGROUND OF THE INVENTION

Lantibiotics are bacterially-produced antimicrobial peptides that possess unique chemical and biological properties owing to their containing a variety of unusual amino acid residues. Lantibiotics are defined as such by the presence of lanthionine or β-methyllanthionine, which are introduced by a posttranslational process in which serine or threonine is dehydrated to the corresponding dehydro residue, which then reacts in a Michael-type addition of a cysteine sulfhydryl group to the double bond of the dehydro residue to form a thioether link. Mature antibiotics typically contain one or more dehydro residues that do not participate in lanthionine bridges. The unique properties that are conferred by these unusual residues results in their being useful components in the design of novel biomolecules.

Nisin is a lantibiotic that is effective against a wide range of gram-positive bacteria. Nisin is a small peptide that is produced by *Lactococcus lactis*, a small bacterium that naturally occurs in milk, and nisin is most stable in acidic conditions. Nisin is also soluble in aqueous environments, but it may be stored at ambient temperatures.

Sublancin, another peptide, is a natural product produced by *B. subtilis* 168. Additionally, sublancin has structural features and physical properties, such as the presence of disulfide bridges and extraordinary stability, that are unprecedented among the known lantibiotics. Sublancin has also proven suitable for the treatment of a bacterial infection. In addition, a bacterial-growth-inhibiting effective amount of sublancin of the invention may be added to a food for preservation against bacteria-mediated spoilage of the food. See U.S. patent application Ser. No. 09/462,478.

Previous methods of inhibiting bacterial outbreaks typically used these lantibiotics separately and their usefulness was limited because the lantibiotics, when used separately, were not effective until after the germination of the spore.

PCT Application WO 99/03352 discloses that a composition comprising a combination of sublancin and nisin would be suitable for killing or inhibiting growth of bacteria (see page 3, lines 8–12, and page 10, lines 4–8). However, there is no disclosure or suggestion regarding the use of the combination for preventing or inhibiting the germination of spores.

Prior art sterilization methods for preventing or inhibiting the germination of spores (such as those using hypochlorite and chlorine dioxide) involve the use of dangerous toxins that require evacuation and quarantine during treatment, and are not at all suitable for use in or around people, animals or food.

Therefore, an improvement is needed over the previous methods that can be used safely both outdoors and indoors, and in and around people, animals and food, without necessitating any evacuation or quarantine during application.

SUMMARY OF THE INVENTION

It has been discovered that when the lantibiotic sublancin is combined with nisin, bacterial spore germination is unexpectedly inhibited.

Nisin and sublancin, when applied separately, are suitable for treating a bacterial infection. In addition, a bacterial-growth-inhibiting effective amount of either of these lantibiotics of the invention may be added to a food for preservation against bacteria-mediated spoilage of the food. However, it has been unexpectedly discovered that the combined application of these lantibiotics results in the inhibition of spore germination altogether, which is a completely different result. It is also possible to apply the nisin and sublancin separately from one another and still achieve the same results as a combined application provided that both the nisin and the sublancin are present when the spore begins to germinate.

Such a combination has many benefits in the commercial world. It can be used to prevent the spread of disease or to counter food-borne pathogens. Additionally, the claimed combination of lantibiotics are also useful in preventing biological attacks by inhibiting the germination of bacterial spores before the spores can develop into their pathogenic state. The claimed combination of nisin and sublancin are an improvement over previous methods because of their unexpected interaction to prevent spore germination, and their relative safety as compared to the poisons previously used for this purpose.

The present invention differs from the disclosure of PCT Application WO 99/03352 in that the present invention inhibits the germination of bacterial spores, while the PCT Application simply discloses killing or inhibiting the outgrowth of bacteria, which occurs after the germination of bacterial spores. Therefore, the present invention is dramatically different from that disclosed in PCT Application WO 99/03352.

Therefore, the present invention is directed towards a method of inhibiting bacterial spore germination comprising contacting bacterial spores with a composition comprising an amount of nisin and an amount of sublancin which, together, are effective to inhibit bacterial spore germination. Additionally, the present invention is directed towards a bactericide, food additive and/or disinfectant, each of which comprises an amount of nisin and an amount of sublancin which, together, are effective to inhibit bacterial spore germination.

Additionally, the present invention is directed towards a method of decontaminating or preventing the contamination of a surface that has been or may be exposed to bacterial spores, said method comprising contacting the surface that has been or may be exposed to the bacterial spores with a composition comprising an amount of sublancin and an amount of nisin, wherein the amounts, together, are effective to decontaminate or prevent contamination of the surface by the bacteria.

The present invention is also directed towards a method for decontaminating or preventing the contamination of food wherein a composition comprising sublancin and nisin in amounts which are together effective to decontaminate or prevent contamination of food is contacted with a surface of a food or incorporated into the food. Additionally, the present invention is directed towards a kit for preventing bacterial spore germination, decontaminating or preventing contamination of surfaces, and/or decontaminating or preventing contamination of food, wherein the kit comprises amounts of sublancin and nisin which, together, are effective for these purposes, and an applicator.

Finally, the present invention is directed towards a method of retarding bacterial spore germination. This method comprises contacting a bacterial spore with a composition comprising nisin and sublancin in amounts effective to retard bacterial spore germination.

DETAILED DESCRIPTION OF THE INVENTION

The present invention is directed to compositions comprising nisin and sublancin in amounts that are effective to inhibit bacterial spore germination. Additionally, the present invention is directed towards methods of inhibiting bacterial spore germination for a variety of purposes.

The term "inhibit" and all variations of this term is intended to encompass the restriction or prohibition of bacterial spore germination after exposure of the inventive composition to bacterial spores.

The term "retard" and all variations of this term is intended to encompass the slowing of the progress of bacterial spore germination.

The term "prevent" and all variations of this term is intended to mean the countering in advance of bacterial spore germination. In other words, this term is intended to encompass the prevention of bacterial spore germination by exposing a surface, food, etc. to the combination of nisin and sublancin prior to the exposure of the surface, food, etc. to bacterial spores.

The lantibiotics of the invention may be incorporated into a composition that is suitable for inhibiting bacterial spore germination or the lantibiotics may be administered separately. The antibiotics are to be provided in amounts effective to prevent bacterial spore germination, decontaminate or prevent contamination of a surface, a food, or any of the other uses recited above. Further, the present invention can be used to retard the outgrowth of bacterial spores by temporarily arresting the germination of the bacterial spores.

Preferably, the amount for inhibiting or preventing bacterial spore germination is between 0.01 to 1000 micrograms of nisin per ml (if a liquid carrier) or mg (if a solid carrier) of carrier and 0.01 to 1000 micrograms of sublancin per ml or mg of carrier. More preferably, the amounts of nisin and sublancin are at least 0.1 micrograms of each per ml or mg of carrier. Another preferred amount is 0.1 micrograms of nisin and 0.4 micrograms of sublancin per ml or mg of the carrier. Also preferred is at least 1.0 microgram of nisin and at least 0.2 micrograms of sublancin per ml or mg of carrier for retarding the germination of bacterial spores. Another preferred amount is 20 micrograms of nisin and 4 micrograms of sublancin. Furthermore, a preferred ratio of nisin to sublancin is 3–7:1, and more preferred is 5:1. All measurements are based on the total volume or weight, respectively, of the carrier, unless otherwise indicated. Suitable carriers are well known in the art. Examples of liquid carriers are water, a salt buffer and the like. Solid carriers include, for example, calcium carbonate, sodium carbonate, lactose and talc. Further carriers which may be used include calcium phosphate and kaolin.

The processes of producing the compositions of the invention are well within the ordinary skill of a worker in the art, and will, therefore, also not be described in detail.

The compositions may be in any form, but an aerosol, solid, liquid, cream or powder form is preferred. Additionally, the liquid form of the compositions can be placed on or embedded in a wipe, said wipe preferably being made of paper or cloth. The present invention may be used against all spore-forming gram positive bacteria, in particular those that are food-borne. Therefore, the present invention is effective against *Clostridium botulinum, Bacillus cereus, Bacillus anthracis, Clostridium tetani, Clostridium perfringens, Bacillus periformis, Clostridium chauvoei, Clostridium haemolyticum, Clostridium novyii, Clostridium septicum, Clostridium sordelli, Bacillus subtilis, Bacillus thuringiensis, Clostridium difficile,* and *Clostridium sporogenes.*

EXAMPLE 1

*Bacillus cereus* T spores were used as the test organisms. *B. cereus* is recognized in the art as being closely related to the *B. anthracis* bacteria. However, unlike *B. anthracis, B. cereus* is non-pathogenic. Therefore, *B. cereus* is an art recognized model for testing agents effective against *B. anthracis.* The ability of nisin and sublancin to inhibit *B. cereus* outgrowth was tested. The nisin was obtained from Aplin and Barrett. Aplin and Barrett sells nisin under the trademark "NISAPLIN™" and the product composition is usually 2.5% nisin, 77.5% sodium chloride, 12% protein, 6% carbohydrate, and 2% moisture. The sublancin was produced in the inventor's laboratory using the method described in U.S. application Ser. No. 09/462,478. Briefly, the sublancin was produced by using a culture of *B. subtills* 168 that was acidified to pH 2.5 with concentrated phosphoric acid, and centrifuged to remove cells. Unbound proteins were then eluted with several volumes of the loading buffer, and the sublancin was eluted with 50 mM NaAc, pH 4.0; or alternatively, with 30% acetonitrile.

The *B. cereus* spores were heat-shocked and outgrown in 2% BACTO® tryptone in the presence of different concentrations of either nisin and sublancin. Inhibitory effects were determined by microscopic examination of the culture using a phase-contrast microscope. In tryptone, phase-bright dormant spores germinated and become phase-dark and the germinated spores then swell, emerge, elongate, and divide. Germination to the phase-dark stage requires about 10 minutes, and division occurs after about an hour. The cells are considered to be vegetative once division has occurred. The events that occur between germination and division are collectively called outgrowth.

In the presence of inhibitory concentrations of either nisin or sublancin, the spores germinate to the phase-dark stage and then become arrested, and do not continue through outgrowth. The nisin and sublancin preparations each arrested outgrowth (allowing the spores to germinate to the phase-dark stage) when present at a concentration of 1 microgram per ml of carrier. This was the minimum amount of each.

EXPERIMENT 2

Following the results of Experiment 1, a second experiment was conducted to see if a combination of nisin and sublancin showed synergy in their inhibitory effect. The expected result was that lower concentrations would result in the same response. However, a different result was obtained. The sample that contained 1 microgram per ml of nisin and 0.2 microgram per ml of sublancin showed inhibition of germination with nearly all of the spores remaining phase-bright. In other words, germination did not occur.

Further, increasing the sublancin content to 0.4 micrograms per ml resulted in a complete inhibition of germination. Additionally, the incubation time (when extended overnight) had no effect on the inhibition. The entire population of spores remained phase bright. Therefore, the present invention has demonstrated a property to inhibit the germination of bacterial spores.

The following references are herein incorporated by reference in their entirety:

1. Hansen, J. N. *Ann. Rev. Microbiol.* (1993) 47, 535–564.
2. Hansen, J. N. (1997) in *Biotechnology of Antibiotics*, Second ed. (Strohl, W. R., ed), pp 437–470, Marcell Dekker, Inc.: New York,
3. Nes, I. F., Tagg, J. R. *Antonie Van Leeuwenhoek* (1996) 69, 89–97.
4. Sahl, H.-G. (1994) in *Antimicrobial Peptides. Ciba Foundation Symposiu6* (Marsh, J., Goode, J. A., eds), pp 27–53, John Wiley & Sons Ltd: Chichester, England,
5. Sahl, H. G., Jack, R. W., Bierbaum, G. *Eur. J. Biochem.* (1995) 230, 827–853.
6. de Vos, W. M., Kuipers, O. P., Vandermeer, J. R., Siezen, R. J. *Mol. Microbiol.* (1995) 17, 427–437.
7. Liu, W., Hansen, J. N. *J. BioL Chem.* (1992) 267, 25078–25085.
8. Chakicherla, A., Hansen, J. N. *J. Bioi. Chem.* (1995) 270, 23533–23539.
9. Kunst, F., Ogasawara, N., Moszer, I., Albertini, A. M., Alloni, G., Azevedo, V., Bertero, M. G., Bessieres, P., Bolotin, A., Borchert, S., Borriss, R., Boursier, L., Brans, A., Braun, M., Brignell, S. C., Bron, S., Brouillet, S., Bruschi, C. V., Caldwell, B., Capuano, V., Carter, N. M., Choi, S. K., Codani, J. J., Connerton, I. F., Danchin, A., et al. *Nature* (1997) 390, 249–256.
10. Feeney, R. E., Garibaldi, J. A., Humphreys, E. M. *Arch. Biochem. Biophys.* (1948) 17, 435–445.
11. Banerjee, S., Hansen, J. N. *J. Biol. Chem.* (1988) 263, 9508–9514.
12. Vary, J. C., Halvorson, H. O. *J. Bacteriol.* (1965) 89, 1340–1347.
13. Meyer, H. E., Heber, M., Eisermann, B., Korte, H., Metzger, J. W., Jung, G. *Anal. Biochem.* (1994) 223, 185–190.
14. Lathe, R. *J. Mol. Biol.* (1985)183, 1–12.
15. Maniatis, T., Fritsch, E. F., Sambrook, J. (1982) *Molecular Cloning. A Laboratory Manual*; Cold Spring Harbor Laboratory, Cold Spring Harbor, N.Y.
16. Liu, W., Hansen, J. N. *J. Bacteriol.* (1991)173, 73877390.
17. Wakamiya, T., Ueki, Y., Shiba, T., Kido, Y., Motoki, Y. *Tetrahedron Lett.* (1985) 26, 665–668.
18. Paik, S. H., Hansen, J. N. *GenBank* (1997) Accession Number AF014938.
19. Meyer, C., Bierbaum, G., Heidrich, C., Reis, M., Suling, J., Iglesias-Wind, M. I., Kempter, C., Molitor, E., Sahl, H.-G. *Eur. J. Biochem.* (1995) 232, 478–489.
20. Havarstein, L. S., Diep, D. B., Nes, I. F. *Mol. Microbiol.* (1995) 16, 229–240.
21. Fisk, C. L. (1975) Ph.D. Thesis, Georgetown University, Washington, D.C.
22. Jones, A. J., Helmerhorst, E., Stokes, G. B. *Biochem. J.* (1983) 211, 499–502.
23. Asquith, R. S., Carthew, P. *Tetrahedron* (1972) 28, 4769–4773.
24. Buchman, G. W., Banerjee, S., Hansen, J. N. *J. Biol. Chem.* (1988) 263, 16260–16266.
25. Kupke, T., Stevanovic, S., Sahl, H. G., Gotz, F. *J. Bacteriol.* (1992) 174, 5354–5361.
26. Cleeland, R., Squires, E. (1991) in *Antibiotics in Laboratory Medicine* (Lorian, V., ed), pp 739–786, Williams & Wilkins: Baltimore, Md.,
27. Liu, W., Hansen, J. N. *Appl. Environ. Microbiol.* (1993) 59, 648–651.
28. Chan, W. C., Dodd, H. M., Horn, N., Maclean, K., Lian, L. Y., Bycroft, B. W., Gasson, M. J., Roberts, G. C. *Appl. Environ. Microbioi.* (1996) 62, 2966–2969.
29. Morris, S. L., Walsh, R. C., Hansen, J. N. *J. Biol. Chem.* (1984) 259,13590–13594.
30. Buchman, G. W. (1988) Ph.D. Thesis, University of Maryland, College Park, Md.
31. Liu, W., Hansen, J. N. *Appl. Environ. Microbiol.* (1990) 56, 2551–2558.
32. Hancock, R. *Lancet* (1997) 349, 418–422.
33. Hancock, R., Falla, T. J. (1997) in *Biotechnology of Antibiotics*, Second ed. (Strohl, W. R., ed), pp 471–496, Marcel Dekker, Inc.: New York,
34. Chan, W. C., Bycroft, B. W., Leyland, M. L., Lian, L. Y., Roberts, G. C. *Biochemistry Journal* (1993) 291, 23–27.
35. Rosenberg, M., Court, D. *Ann. Rev. Genetics* (1979) 13, 319–353.
36. Kozak, M. *Microbiol Rev.* (1983) 47, 1–45.
37. U.S. application Ser. No. 09/462,478
38. PCT Application WO 99/03352

What is claimed:

1. A method of inhibiting bacterial spore germination, said method comprising contacting said bacterial spore with a composition comprising nisin and sublancin in amounts effective to inhibit bacterial spore germination, and a carrier.

2. The method of claim 1, wherein the bacteria is *Clostridium botulinum*.

3. The method of claim 1, wherein the bacteria is *Bacillus cereus*.

4. The method of claim 1, wherein the bacteria is *Bacillus anthracis*.

5. The method of claim 1, wherein the bacteria is a food-borne pathogen.

6. The method of claim 1, wherein the bacteria is selected from the group consisting of *Clostridium botulinum, Bacillus cereus, Bacillus anthracis, Clostridium tetani, Clostridium perfringens, Bacillus periformis, Clostridium chauvoei, Clostridium haemolyticum, Clostridium novyil, Clostridium septicum, Clostridium sordelli, Bacillus subtilis, Bacillus thuringiensis, Clostridium difficile*, and *Clostridium sporogenes*.

7. A composition suitable for inhibiting bacterial spore germination comprising an amount of nisin and an amount of sublancin which are together effective to inhibit bacterial spore germination, and a carrier.

8. The composition of claim 7, wherein said composition is in liquid form.

9. The composition of claim 7, wherein said composition is in a powder form.

10. The composition of claim 7, wherein said composition is in aerosol form.

11. A method of preventing bacterial spore germination, said method comprising contacting a surface prior to exposure to bacteria with a composition comprising nisin and sublancin in amounts effective to prevent bacterial spore germination, and a carrier.

12. The method of claim 11, wherein the spore forming bacteria is selected from the group consisting of *Clostridium botulinum, Bacillus cereus, Bacillus anthracis, Clostridium tetani, Clostridium perfringens, Bacillus periformis, Clostridium chauvoei, Clostridium haemolyticum, Clostridium novyii, Clostridium septicum, Clostridium sordelli, Bacillus subtilis, Bacillus thuringiensis, Clostridium difficile*, and *Clostridium sporogenes*.

13. A method of retarding bacterial spore germination, said method comprising contacting said bacterial spore with a composition comprising nisin and sublancin in amounts effective to retard bacterial spore germination, and a carrier.

* * * * *